United States Patent [19]
DeVaney, Jr. et al.

[11] Patent Number: 5,089,233
[45] Date of Patent: Feb. 18, 1992

[54] PROCESSING APPARATUS FOR A CHEMICAL REACTION PACK

[75] Inventors: Mark J. DeVaney, Jr.; John S. Lercher; Jeffrey A. Wellman, all of Rochester, N.Y.

[73] Assignee: Eastman Kodak Company, Rochester, N.Y.

[21] Appl. No.: 452,666

[22] Filed: Dec. 18, 1989

Related U.S. Application Data

[63] Continuation-in-part of Ser. No. 365,079, Jun. 12, 1989, abandoned.

[51] Int. Cl.⁵ .............................................. B01L 9/00
[52] U.S. Cl. ................................ 422/99; 100/93 RP; 100/210; 206/219
[58] Field of Search ................... 422/99; 222/101, 102, 222/146.2, 52, 53, 54; 100/210, 92, 93 RP, 288, 289, 38; 206/219

[56] References Cited

U.S. PATENT DOCUMENTS

| | | | |
|---|---|---|---|
| 1,798,555 | 3/1931 | Pipkin | 100/210 |
| 3,036,894 | 5/1962 | Forestiere | 436/165 |
| 4,038,030 | 7/1977 | Albright et al. | 436/165 |
| 4,234,104 | 11/1980 | Apuzzo, Jr. et al. | 222/101 |
| 4,236,806 | 12/1980 | Hoadley | 354/303 |
| 4,654,127 | 3/1987 | Baker et al. | 204/153.1 |
| 4,673,657 | 6/1987 | Christian | 436/501 |
| 4,795,265 | 1/1989 | Dahlberg et al. | 206/219 |

Primary Examiner—Robert J. Warden
Assistant Examiner—Laura E. Collins
Attorney, Agent, or Firm—Dressler, Goldsmith, Shore, Sutker & Milnamow, Ltd.

[57] ABSTRACT

An apparatus for transferring liquid from one chamber to another in successive chambers of a chemical reaction pack comprising a support surface and pressure applicators. Temperature control elements are also provided to heat and cool the liquid contained within the chemical reaction pack.

10 Claims, 4 Drawing Sheets

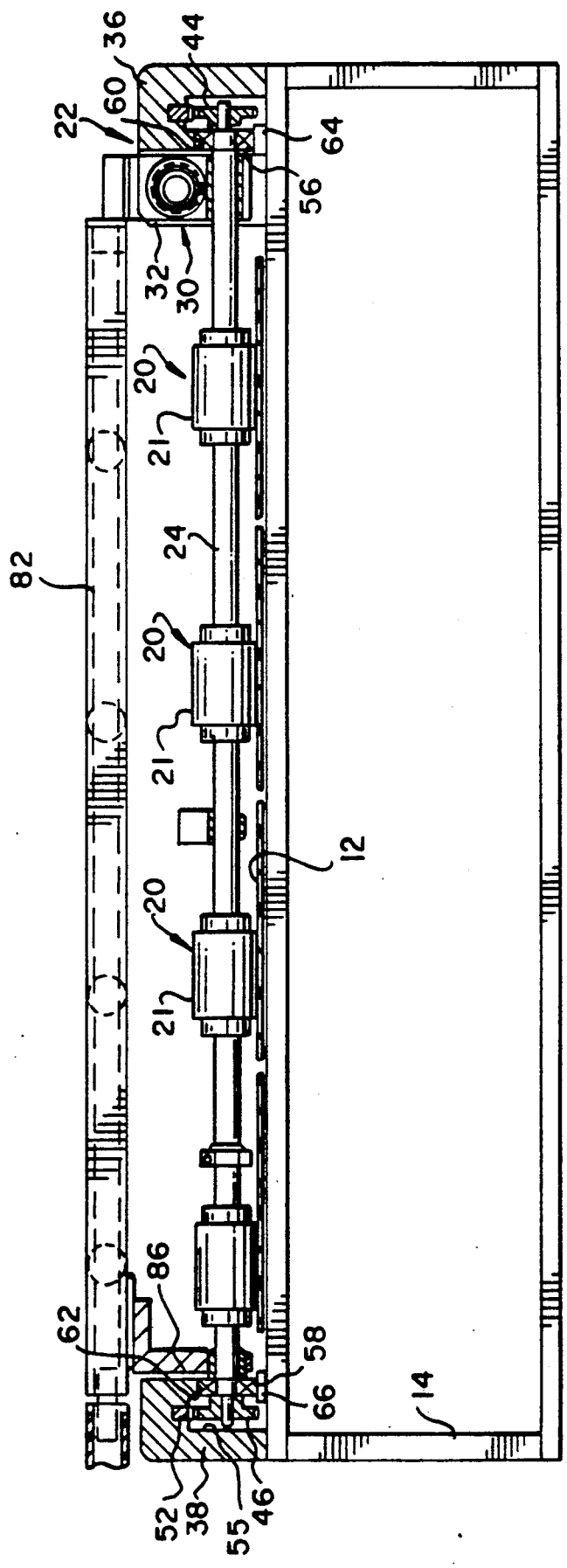

PROCESSING APPARATUS FOR A CHEMICAL REACTION PACK

RELATED APPLICATIONS

This is a continuation-in-part application of U.S. Ser. No. 365,079 filed on June 12, 1989, now abandoned.

FIELD OF THE INVENTION

The present invention relates to a processing apparatus for progressively transferring a test fluid between adjacent chambers of a chemical reaction pack.

BACKGROUND OF THE INVENTION

Disposable reaction packs for use in automatic analysis equipment are known in the art. Such reaction packs typically comprise a body fabricated from flexible pliable material. The body of the reaction pack is divided into successive individual compartments or chambers having blister-like configurations that are normally separated from each other with seals which are rupturable or openable in response to a sufficient pressure being applied to such seals. One or more of the compartments or chambers contain predetermined amounts of reagents with which a test liquid reacts.

By applying an external linearly advancing pressure to the blister-like chambers, the normally closed seals are opened to permit transfer of the contents of a preceding chamber to a succeeding chamber. The transfer of the test liquid between chambers and the intermixing thereof with the reagents is preferably accomplished without opening the reaction pack.

Manually applying an external pressure to each blister-like chamber of the reaction pack to establish sufficient internal pressure to open the normally closed seal is tedious, time-consuming, inexact, and could result in damage to the reaction pack. Inconsistency or variations in pressure and time can adversely effect chemical reactions within the pack and lead to inaccurate results. It would be beneficial, therefore, to automate the process of facilitating transfer of test liquids through a reaction pack.

The test liquids in the reaction pack may be subjected to temperature changes during the test procedure. It has been found, for example, that thermal cycling by heating and cooling a metal block on which a reaction pack is situated is relatively slow and inefficient. Accordingly, there is a need and desire for a device which automatically transfers a test liquid through a reaction pack with consistency while facilitating heating and cooling thereof to treat the liquids contained therewithin.

SUMMARY OF THE INVENTION

In view of the above, and in accordance with the present invention, there is provided a processing apparatus for facilitating progressive transfer of a test liquid between adjacent chambers of a chemical reaction pack. The processing apparatus further includes temperature-control elements for heating and cooling the test liquid within the chemical reaction pack as the test liquid is transferred therethrough.

The processing apparatus of the present invention includes a support surface on which the chemical reaction packs are horizontally supported. One or more pressure applicators are provided above the support surface. A drive mechanism moves the pressure applicators across the reaction pack to transfer the test liquid between adjacent chambers of the reaction pack.

In a preferred form, the support surface is sized to horizontally support a plurality of disposable reaction packs in side-by-side and end-to-end relation relative to each other. The support surface is preferably apertured to permit a temperature-control unit to heat and cool the test liquid from opposite sides of the reaction pack.

In their simplest form, the pressure applicators include a series of rollers which are arranged endwise on a shaft forming part of the drive mechanism. The drive mechanism advances the shaft with the rollers across the support surface while maintaining a substantially constant orientation between the shaft and the support surface.

In a preferred form, the drive mechanism comprises a bracket supported at one end of the shaft and an axially elongated worm gear which extends in a direction generally orthogonal to the shaft and threadably engaging the bracket. The drive mechanism further includes a device for rotatably driving the worm gear to move the shaft. A rack and pinion arrangement is provided at opposite ends of the shaft. As the shaft moves, it is maintained generally perpendicular to the axis of the reaction packs irrespective of where the driving force is applied by the worm gear and which of the rollers runs into resistance from the blister-like chambers on the reaction pack.

In a preferred form, each rack and pinion arrangement comprises a gear rack extending generally orthogonal to the shaft and a pinion gear intermeshing with the rack and fixed on the shaft. The drive mechanism may further include a bearing carried by the shaft for facilitating accurate positioning of the rollers relative to the support surface as the rollers move across the reaction pack.

To promote temperature changes of the liquids within the disposable reaction pack, temperature-controlling elements are mounted for movement in front of and with the rollers. Each temperature-controlling element includes upper and lower units. In a start position, the upper unit of the temperature-controlling element is positioned above a similar unit disposed beneath the support surface so that the two units can work together to provide the necessary heating and cooling cycle for the liquids in the reaction pack. When the rollers are moved, the upper unit is moved with the rollers and is positioned over the next blister-like chamber in the reaction pack. After the start position, all subsequent chambers in the reaction pack are treated by the temperature-control element from the top only. As will be understood, heating may either be at a constant temperature or a heating/cooling cycle.

The apparatus of the present invention allows each of the reaction packs arranged on the support surface to be treated with constant pressures on a generally flat surface for uniform time periods. Moreover, the present invention automates and simplifies handling of chemical reaction packs. When a temperature-control element is arranged in combination therewith, temperature of the test liquid in the reaction packs can be controlled during transfer of the test liquid between chambers.

Numerous other features and advantages of the present invention will become apparent from the following detailed description, the accompanying drawings, and the appended claims.

BRIEF DESCRIPTION OF THE DRAWINGS

FIG. 2 is a side sectional view taken along line 2—2 of FIG. 1;

DETAILED DESCRIPTION OF A PREFERRED EMBODIMENT

Figure 1:
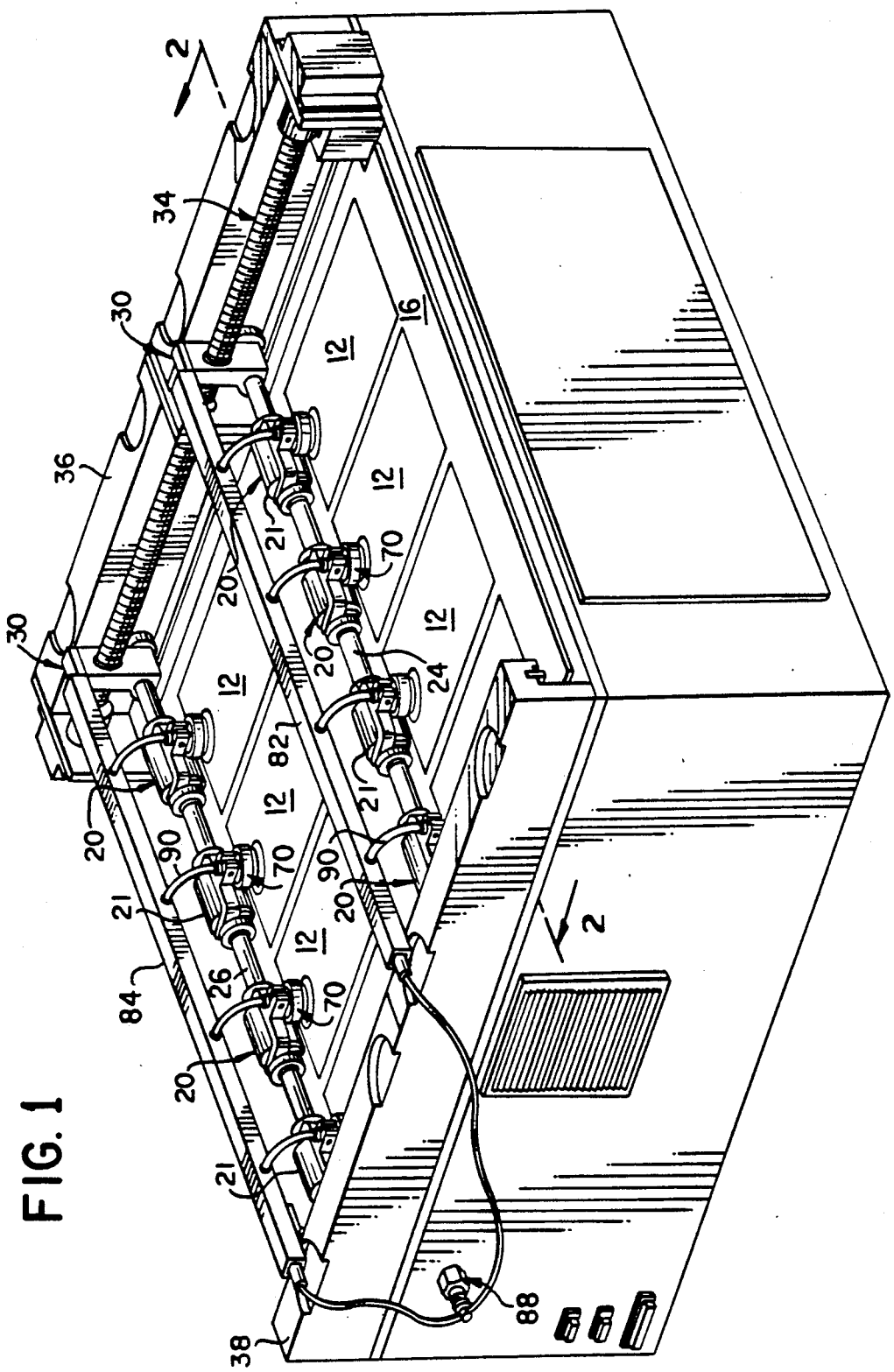
FIG. 1 is a perspective view of an apparatus embodying principles of the present invention and which is capable of operating upon a plurality of chemical reaction packs.

While the present invention is susceptible of embodiment in various forms, there is shown in the drawings and will hereinafter be described a presently preferred embodiment with the understanding that the present disclosure is to be considered as an exemplification of the invention, and is not intended to limit the invention to the specific embodiment illustrated.

Referring now to the drawings, wherein like reference numerals refer to like parts throughout the several views, there is illustrated an apparatus 10 for operating on one or more chemical reaction packs 12. Each chemical reaction pack 12 comprises a sealed hollow body formed from fluid impermeable pliable material which is separated or divided into a series of aligned chambers; with each chamber having a blister-like configuration. A test liquid is contained within one of the chambers and suitable reagents are contained within other chambers.

A more detailed description of a preferred form of reaction pack is provided in commonly assigned and pending U.S. patent application filed concurrently herewith, entitled "Temperature Control Device and Reaction Vessel", which is also a continuation-in-part of U.S. Ser. No. 365,079; the full teachings of which are incorporated herein by reference.

Figure 4:
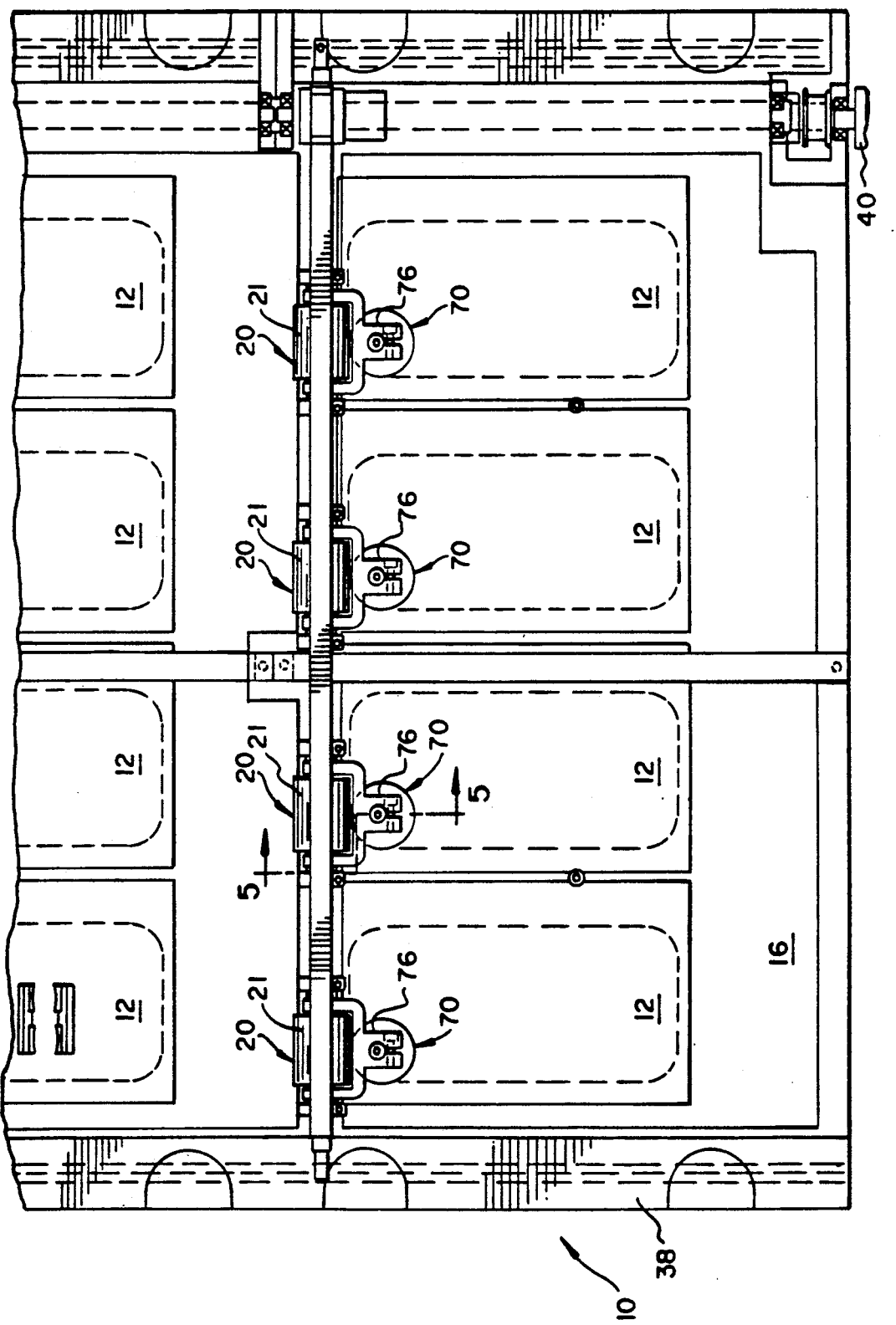
FIG. 4 is a top plan view of the apparatus of the present invention.

The apparatus 10 of the present invention is preferably constructed as a self-contained unit including a base assembly 14 having a supporting surface 16 for supporting the chemical reaction packs 12 thereon in a substantially horizontal plane. As illustrated in FIGS. 1 and 4, support surface 16 is preferably sized to accommodate a plurality of chemical reaction packs 12 in side-by-side and end-to-end relation relative to each other.

Apparatus 10 includes pressure applicators 20 arranged above the support surface 16 of base assembly 14. In a preferred form, each pressure applicator 20 comprises a roller 21 located a predetermined distance above the support surface 16 for applying external pressure to a reaction pack 12 to transfer the liquid contained in the pack from one chamber to another.

Each roller 21 is moved through a range of movement extending endwise across the reaction packs by a drive mechanism 22. As best illustrated in FIG. 2, drive mechanism 22 includes an elongated shaft 24 extending above and laterally across the support surface 16. A first series of rollers 21 are arranged endwise and freely rotatable on shaft 24.

To facilitate an increase in the capacity of the apparatus 10, another elongated shaft 26 (FIG. 1) extends above and laterally across the support surface 16. Shafts 24 and 26 extend substantially parallel to each other and to the support surface 16. A second series of rollers 21 are arranged endwise and freely rotatable on shaft 26.

The drive mechanism 22 moves the shafts 24 and 26 with the rollers 21 mounted thereon across support surface 16. In a preferred form, the drive mechanism 22 conjointly moves both shafts 24 and 26 and the rollers supported thereon. The apparatus can be readily modified to operate shaft 24 with a first series of rollers 21 supported thereon independently of shaft 26 which has a second series of rollers 21 supported thereon.

Figure 3:
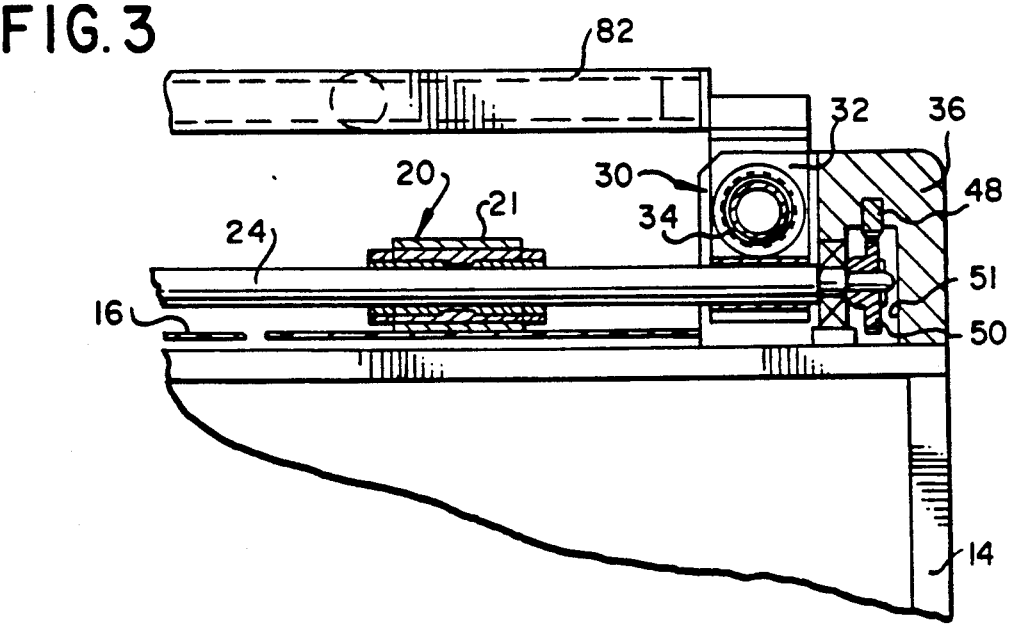
FIG. 3 is an enlarged view of a portion of a drive mechanism forming part of the present invention.

The drive mechanism 22 and its relative association with shaft 24 will be described in detail with the understanding that similar construction is provided for shaft 26 and/or other shafts which support rollers 21 thereon. As illustrated in FIG. 3, the drive mechanism 22 includes a non-rotatable bracket 32 supported at one end of shaft 24. An axially elongated worm gear 34 extends in a direction generally orthogonal to the shaft 24 and threadably engages and passes through bracket 32. Opposite ends of the worm gear 34 are rotatably journalled in opposite ends of an upstruck support 36 connected to the base assembly 14 and extending generally parallel to the worm gear 34. Another upstruck support 38 (FIG. 2) similar to support 36 is provided at the opposite end of shaft 24. A motor 40 (FIG. 1) is fixedly supported on base assembly 14 for rotatably driving the worm gear 34 in opposite directions to effect linear movement of the shaft 24, thereby moving rollers 21 through their range of movement across the support surface 16.

The drive mechanism 22 is designed to facilitate programming of the apparatus and to allow each of the rollers 21 co-equally act on each reaction pack 12 during their range of movement. To effect such ends, and as illustrated in FIG. 2, drive mechanism 22 includes rack and pinion assemblies 44 and 46 arranged at opposite ends of shaft 24 and extending substantially perpendicular or orthogonal thereto.

Alternatively, packs 12 can be operated upon randomly, if so desired.

As illustrated in FIG. 3, rack and pinion assembly 44 includes a gear rack 48 and a pinion gear 50 accommodated within a cavity 51 defined in support 36. Gear rack 48 is arranged endwise on support 36 and extends parallel to the worm gear 34. Pinion gear 50 is pinned or otherwise affixed to one end of shaft 24.

Similarly, and as illustrated in FIG. 2, rack and pinion assembly 46 includes a gear rack 52 and a pinion gear 54 accommodated within a cavity 55 defined in support 38. Gear rack 52 is arranged on support 38 and extends parallel to gear rack 48. Pinion-- gear 54 is pinned or otherwise affixed to the opposite end of shaft 24.

Drive mechanism 22 further comprises bearings 56 and 58 provided at opposite ends of shaft 24. As illustrated in FIG. 2, bearings 56 and 58 are entrapped between upper guide faces 60 and 62 defined on supports 36 and 38, respectively, and elongated lower rails 64 and 66, respectively. Each rail 64 and 66 is fixed relative to the support surface 16. Accordingly, the horizontal axis of shaft 24 about which rollers 21 move during their range of movement is maintained substantially parallel to and in a constant orientation with the support surface 16.

The apparatus 10 of the present invention further includes a plurality of temperature-controlling elements 70 for providing rapid temperature changes in the fluid contained within the reaction pouch. As illustrated in FIG. 1, a first series of temperature-controlling elements 70 are associated with shaft 24, while a second series of temperature-controlling elements 70 are associated with shaft 26. Each temperature-controlling element 70 is efficient, inexpensive and capable of rapidly moving the temperature of 140 $\mu$l of liquid from 95° C. to 55° C. to 70° C. and back to 95° C. in a time period of from 0.75 minutes to 1.75 minutes, with a dwell time of at least 3 seconds at each of said temperatures.

Figure 5:
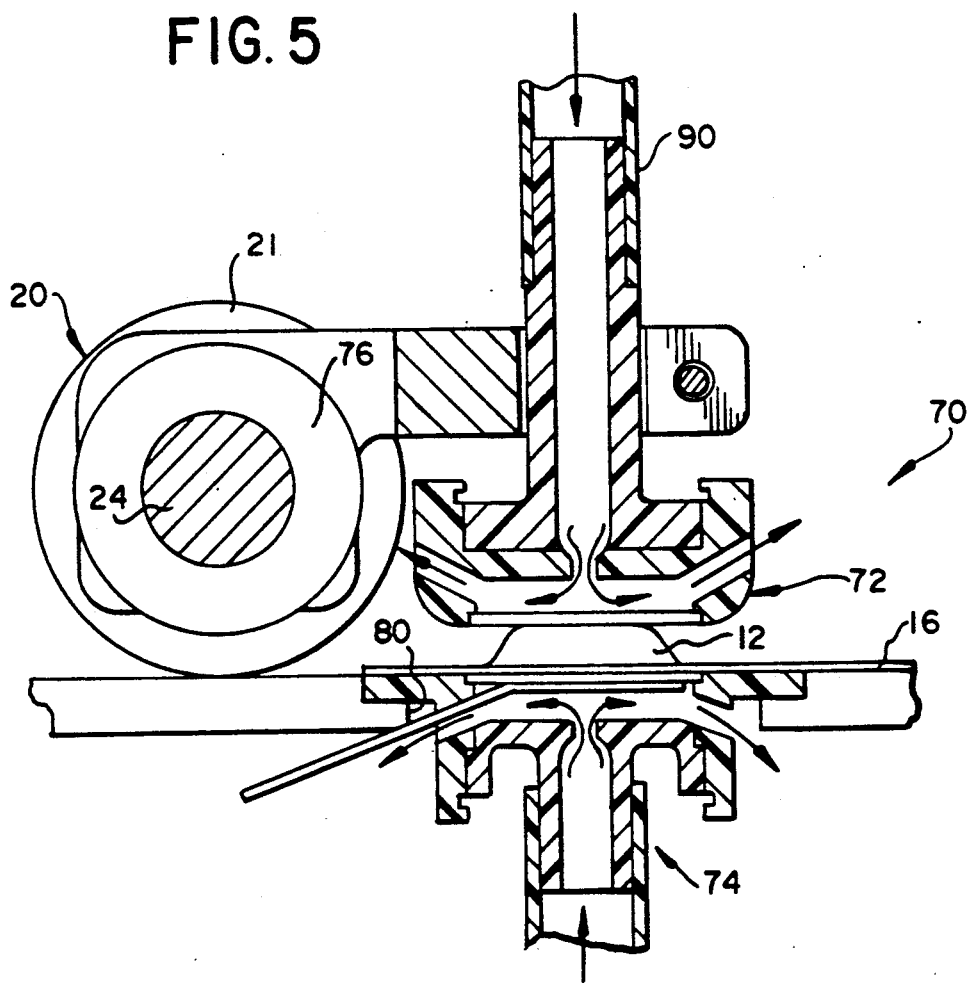
FIG. 5 is an enlarged sectional view taken along line 5—5 of FIG. 4.

Turning to FIG. 5, in a preferred form, each temperature-control element 70 includes an upper unit 72 and a lower unit 74. Each upper unit of the temperature-control elements 70 is supported in substantially the same manner. Accordingly, only a temperature-control element 70 as mounted to shaft 24 will be described in detail. Each upper unit 72 is carried in advance of and in alignment with a pressure applicator 20. A suitable cantilevered bracket 76 serves to mount the upper unit 72 to the shaft 24. Accordingly, when the pressure applicator 20 is moved through its range of movement the upper unit 72 of the temperature control element 70 moves therewith.

As illustrated in FIG. 5, the support surface 16 defines a series of apertures 80 (only one of which is shown) which permit the lower heating unit 74 of the temperature control element to provide the necessary heating cycle to a lower surface of the chemical reaction pack 12. Additional heaters (not in the path of the pressure applicators 20) are provided as necessary for areas of the reaction pack that must be maintained at substantially constant temperature to receive the liquid warmed by the upper heater unit 72.

As illustrated in FIGS. 1 and 2, a pair of elongated tubular members 82 and 84 extend generally parallel to and in vertically spaced relation with shafts 24 and 26, respectively. The tubular members 82 and 84 are supported at one end by the non-rotatable brackets 32 of the drive mechanism 22. Support members 86 and 87, which are carried by the respective shafts 24 and 26, vertically support the other end of tubes 82 and 84. Accordingly, tubes 82 and 84 move with the respective shaft as the pressure applicators 20 move through their range of movement.

Tube 82 and 84 are connected to a source of cooling air 88 (FIG. 1). Moreover, tubes 82 and 84 have a series of conduits 90 (FIGS. 1 & 5) which direct the cooling air from the tubes 82 and 84 to the various temperature-control elements 70 to provide the gradients in temperatures required.

Base assembly 14 further contains a computer, temperature measurement circuits, heater and motor drive circuits, and power supplies. A computer program controls functioning of the apparatus 10 and allows for changes to the operating parameters. An internal filter/regulator and solenoid valve will provide control to the air directed to the temperature-control element 70.

Transfer of the reagents in the chambers of the reaction packs is achieved by the action of the pressure applicators 20 against the blister-like chambers in the reaction packs. In the start position, the upper and lower units 72 and 74 of each temperature-control element 70 are positioned to provide the necessary heating and cooling cycle for the liquid in the reaction pack. As the pressure applicators 20 linearly move through their range of movement, each roller 21 applies an external pressure against the reaction pack to transfer the liquid from one chamber to an adjacent chamber. Moreover, as the pressure applicators are moved, the upper unit 72 of each temperature-control unit 70 is pushed before the pressure applicator and is positioned over a succeeding chamber in the reaction pack that requires heating. After the start position, all subsequent chambers in the reaction packs are heated from the top only.

To effect movement of the pressure applicators 20 in either direction, motor 40 is suitably operated to rotatably drive the worm gear 34. Engagement between worm gear 34 and each of the non-rotatable brackets 32 in the drive mechanism 30 causes linear displacement of the brackets and thereby the shafts 24 and 26 connected thereto.

To simplify control of the apparatus 10 and to ensure that corresponding chambers in each reaction pack are activated simultaneously for an equivalent time period, drive mechanism 22 is designed such that shafts 24 and 26 and the pressure applicators 20 carried thereby maintain a substantially constant orientation relative to the support surface 16. The rack and pinion assemblies 44 and 46 associated with each shaft 24 and 26 of the drive mechanism are provided to effect such ends. Each gear rack 48 and 52 is held stationary above the support surface 26. Each pinion gear 50 and 54 which intermeshes with the racks 48 and 52, respectively, is therefore caused to rotate upon linear movement of the shafts 24 and 26 with the rollers 21 attached thereto. Because each pinion gear is affixed to an end of a respective shaft, rotational movement imparted to the pinion gear is likewise imparted to the shaft. Accordingly, each shaft is positively driven at both ends and is maintained substantially perpendicular to the longitudinal axis of the packets regardless of where a driving force is applied thereto and regardless of which of the rollers 21 carried thereon runs into resistance from the reaction pouch.

Moreover, the bearings 56 and 58 arranged at opposite ends of each shaft 24 and 26 further promote and maintain a substantially constant orientation between the pressure applicators 20 and the support surface 16. The ability to maintain a constant orientation between the pressure applicators 20 and the support surface 16 simplifies the control of the apparatus 10 and allows each of the packs to be coequally acted upon for equal time periods, thereby facilitating handling of the reaction packs.

From the foregoing, it will be observed that numerous modifications and variations can be effected without departing from the true spirit and scope of the novel concept of the present invention. It will be appreciated that the present disclosure is intended to set forth exemplifications of the invention which are not intended to limit the invention to the specific embodiments illustrated. The disclosure is intended to cover by the appended claims all such modifications as fall within the scope of the claims.

What is claimed is:

1. A processing apparatus for transferring a liquid between chambers of a chemical reaction pack having blister-like chambers formed therein, comprising:
   a support surface for supporting a chemical reaction pack in a substantially horizontal plane;
   pressure applicators supported above said support surface for acting on said reaction pack to transfer fluid between adjacent chambers;
   means for operating said pressure applicators through a range of movement extending across said reaction pack, said operating means comprising a shaft having said pressure applicators arranged thereon and which advances said pressure applicators across the support surface while maintaining a substantially constant orientation between said pressure applicators and said support surface; and temperature-control elements movable with said pressure applicators and operable upon said reaction pack.

2. The processing apparatus according to claim 1 wherein said operating means further comprises a non-rotatable bracket supporting one end of said shaft, an axially elongated worm gear extending in a direction generally orthogonal to said shaft and threadably engaging said bracket, and means for rotatably driving said worm gear.

3. The processing apparatus according to claim 1 wherein said operating means further includes rack and pinion means arranged at opposite ends of said shaft for ensuring that the shaft advances across said support surface while maintaining a substantially constant orientation with said support surface throughout the range of movement of said pressure applicators.

4. The processing apparatus according to claim 3 wherein said rack and pinion means comprises a gear rack extending generally orthogonal to said shaft, and a pinion gear intermeshed with said rack and mounted on said shaft.

5. The apparatus according to claim 1 wherein said operating means further includes bearing means carried by said shaft for facilitating movement of said shaft across said support surface while maintaining a substantially constant orientation between said shaft and said support surface.

6. A processing apparatus for transferring a fluid between blister-like chambers in a chemical reaction pack, comprising:

a support surface for supporting a plurality of chemical reaction packs in side-by-side and end-to-end relation relative to each other;

a plurality of rollers supported above said support surface and in alignment with blister-like chambers on said reaction packs;

drive mechanism means for moving said rollers across said support surface to operate against said reaction packs and facilitate transfer of fluid therethrough, said drive mechanism means comprising at least two spaced apart generally parallel shafts with a first series of rollers arranged endwise on a first shaft and a second series of rollers arranged endwise on a second shaft, and wherein said drive mechanism means advances said shafts with said rollers arranged thereon across said support surface while maintaining a substantially constant orientation relative to said support surface; and temperature-control means carried in advance of said rollers for thermally treating the fluid transferred through said reaction pack.

7. The processing apparatus according to claim 6 wherein said support surface is apertured to accommodate temperature-control elements beneath said reaction packs.

8. The processing apparatus according to claim 6 wherein said drive mechanism means comprises a non-rotatable bracket arranged at one end of each shaft, an axially elongated and rotatable worm gear passing through and engaging each of said brackets, and means for rotatably driving said worm gears.

9. The processing apparatus according to claim 6 wherein said drive mechanism means further includes rack and pinion means arranged at opposite ends of each shaft for facilitating advancement of said shafts across the support surface while maintaining a substantially constant orientation relative to said support surface, each rack and pinion means comprising a gear rack extending substantially perpendicular to the respective shaft, and a pinion gear mounted at an end of the respective shaft to intermesh with said gear rack.

10. The apparatus according to claim 6 wherein said drive mechanism means further includes a rail adjacent to said gear rack and fixedly arranged relative to said support surface, and bearing means carried by said shaft such that said bearing means rides on said rail.

* * * * *